(12) United States Patent
Filbry et al.

(10) Patent No.: US 8,529,921 B2
(45) Date of Patent: Sep. 10, 2013

(54) POLYAMIDE-5 COMPOUNDS IN COSMETIC PREPARATIONS

(75) Inventors: Alexander Filbry, Hamburg (DE);
Rainer Kroepke, Schenefeld (DE);
Silke Heinecke, Hamburg (DE);
Alexandra Blohm, Hamburg (DE); Jens Nielsen, Hamburg (DE)

(73) Assignee: Beiersdorf AG, Hamburg (DE)

( * ) Notice: Subject to any disclaimer, the term of this patent is extended or adjusted under 35 U.S.C. 154(b) by 23 days.

(21) Appl. No.: 13/123,740

(22) PCT Filed: Oct. 12, 2009

(86) PCT No.: PCT/EP2009/007306
§ 371 (c)(1),
(2), (4) Date: Jun. 17, 2011

(87) PCT Pub. No.: WO2010/043351
PCT Pub. Date: Apr. 22, 2010

(65) Prior Publication Data
US 2011/0268674 A1      Nov. 3, 2011

(30) Foreign Application Priority Data
Oct. 13, 2008   (DE) .......................... 10 2008 051 007

(51) Int. Cl.
*A61K 8/02* (2006.01)

(52) U.S. Cl.
USPC .................. 424/401; 424/70.17; 514/937

(58) Field of Classification Search
USPC ................. 424/70.17, 401; 514/937
See application file for complete search history.

(56) References Cited

U.S. PATENT DOCUMENTS

| | | |
|---|---|---|
| 5,955,060 A | 9/1999 | Huglin et al. |
| 5,994,445 A | 11/1999 | Kaschel et al. |
| 6,248,311 B1 | 6/2001 | Candau |
| 6,274,124 B1 | 8/2001 | Vollhardt |
| 6,403,704 B1 | 6/2002 | Bara |
| 6,620,407 B1 | 9/2003 | Gers-Barlag et al. |
| 2005/0196347 A1* | 9/2005 | Berillouet et al. .............. 424/47 |
| 2005/0197446 A1 | 9/2005 | Loyen et al. |
| 2006/0041041 A1 | 2/2006 | Douais et al. |
| 2006/0115504 A1 | 6/2006 | Loyen et al. |
| 2006/0205883 A1 | 9/2006 | Loyen et al. |

FOREIGN PATENT DOCUMENTS

| | | |
|---|---|---|
| DE | 198 34 819 A1 | 2/2000 |
| DE | 100 28 718 A1 | 12/2001 |
| DE | 10 2006 040 903 A1 | 3/2008 |
| EP | 0 818 508 A | 1/1998 |
| EP | 1 078 638 A | 2/2001 |
| WO | 97/30679 A | 8/1997 |
| WO | 2008/101692 A | 8/2008 |
| WO | WO-2008/101692 A2 * | 8/2008 |
| WO | 2008/145889 A | 12/2008 |

OTHER PUBLICATIONS

Arkema, Orgasol Caresse: New Senses for Skin Care, Jun. 15, 2007.*
Anonymous: "Orgasol Caresse"[Online] Mar. 2007, pp. 1-8, XP002541559 Retrieved from the Internet: URL:http://web.archive.org/web/20071022051 032/http://www.arkema.com/pdf/E N/products/technical_polymers/orgasol/BROC HURE_ORGASOL_CARESSE.pdf> [retrieved on Aug. 14, 2009].
Anonymous: "Orgasol—Cosmetic Ingredients" Internet Citation, [Online] Mar. 1, 2008, pp. 1-8, XP002528387 Retrieved from Internet: URL:http://www.arkema.com/pdf/EN/products/technical_polymers/orgasol/broc hure_Orgasol_cosmetics_2008.pdf> [retrieved on May 14, 2009].
Chemical Abstracts, vol. 54, No. 2, Jan. 6, 2005, Columbus, Ohio, US; abstract No. 2005:9521, K. Kawakami: "Oil-in-water cosmetic emulsions containing sphingosines, acids, ceramides, and hydrophobic powders" XP002569460 -& JP 2005 002022 A (Kao Corp) Jan. 6, 2005.
Valerie Parison: "Active delivery from Nylon particles" Cosmetics & Toiletries, Wheaton, IL, US, vol. 108, No. 12, Dec. 1, 1993, pp. 97-100, XP002085590 ISSN: 0361-4387.
English language abstract of EP 0878469 A1, published Nov. 18, 1998.
Parfums Cosmetique—N 198—Dec. 2007 on Internet: http://www.arkema.com/pdf/EN/products/technical_polymers/orgasol/PCA 198_Arkema.pdf.

* cited by examiner

*Primary Examiner* — Ali Soroush
(74) *Attorney, Agent, or Firm* — Abel Law Group, LLP

(57) ABSTRACT

Polyamide-5 compounds show an increase of the care and/or efficacy properties of cosmetic or dermatological preparations, such as waterproofness, long-term stability, skin moisture and stickiness. The preparations preferably comprise one or more care agents or active ingredients selected from the group of UV filter substances, anti-wrinkle active ingredients, skin moisturizers and/or lipids.

20 Claims, No Drawings

POLYAMIDE-5 COMPOUNDS IN COSMETIC PREPARATIONS

BACKGROUND OF THE INVENTION

1. Field of the Invention

The invention comprises the use of one or more polyamide-5 (Orgasol Caresse) to increase the care and/or efficacy properties of cosmetic or dermatological preparations, such as water proofness, long-term stability, skin moisture and stickiness.

2. Discussion of Background Information

Nylon is a 100% synthetic fiber, which was first introduced by Du Pont in 1939. Nylon has been adopted as a generic name for linear, aliphatic polyamides. Thus Nylon 4, Nylon 11, etc. designate chemically correctly polyamide/polyamide fibers PA4, PA11.

The original Nylon is chemically a PA66, i.e., a polycondensation product of hexane-1,6-diamine and adipic acid.

In cosmetics, Nylon types 6, 11, 12 and 66 as well as Nylon copolymers 12, 6, 66 are known. These Nylon types have in particular swelling properties, i.e., reduce the bulk density of cosmetic agents, opacifying properties, i.e., reduce the transparency and the light transmittance of cosmetic agents, and viscosity-regulating properties, i.e., increase or reduce the viscosity of cosmetic agents.

Nylon types 6-14 are known from Arkema under the trade names Orgasol® and Orgasol Caresse®. The production of these polyamide types, in particular PA 6, PA6-6, PA 12, PA 6-12 and PA 6-14, is described in US 20050197446, US 20060041041 and US 20060205883 of Arkema.

Orgasol Caresse® thereby represents the polyamide-5 compounds according to INCI, which can be used, for example, to increase the sunscreen factor in cosmetic sunscreen products (parfums cosmetique, no. 198, December 2007, p. 72).

Orgasol types are available as ultra-fine powders, with in part small particle sizes. The use is known in foundations, lipsticks, mascara, eye shadows and nail polishes, likewise in gel creams, skin moisturizing agents, lotions, sunscreen preparations or after-shave formulations.

The Nylon-6 types are lipophilic and make it possible for the preparations containing it to have a silky feeling on the skin. Nylon-12 types are less lipophilic and impart a dry feeling on the skin.

Orgasol Caresse®, also sold as Orgasol Type 4000 EXD, was specifically developed for aqueous formulations. It comprises fine polyamide copolymer (6-12) powder with an average particle size of 10 Orgasol Caresse® has a higher absorption capacity for water as well as for oil compared to the other Orgasol types.

It thus renders possible the better dispersibility of the cosmetic preparations and gives the preparation a certain richness, even with a small oil phase.

Sunscreen preparations contain a UV filter, which filters certain UV rays out of sunlight in order to protect the skin or the hair from their harmful effects. Known UV filters are substances from the positive list of the UV filters (Annex VII of the EC Cosmetics Directive) and are preferably used.

A measure of the effectiveness of UV protection is represented for the purposes of the present invention for example by the sun protection factor (SPF).

The sun protection factor (SPF) indicates the increased time of exposure to the sun's rays made possible through use of the sunscreen composition. It is the ratio of the erythema threshold time with sunscreen composition to erythema threshold time without sunscreen composition.

The effectiveness of UV-A protection is normally tested by using the IPD method (IPD=immediate pigment darkening). This involves—similar to the determination of the sun protection factor—the determination of a value which indicates how much longer skin protected with the light protection composition can be exposed to UV-A radiation until the same pigmentation occurs as with the unprotected skin.

Another test method which has become established throughout Europe is the Australian standard AS/NZS 2604: 1997. This involves the measurement of the absorption of the preparation in the UV-A range. To comply with the standard, the preparation must absorb at least 90% of the UV-A radiation in the range from 320 to 360 nm.

In general, the light absorption behavior of light-protective filter substances is very well known and documented, especially as there are positive lists for the use of such substances in most industrialized countries, which impose very strict standards on the documentation.

The use concentration of known light-protective filter substances present in the form of a solid, is, however, often limited—especially in combination with other substances to be dissolved. This therefore gives rise to certain technical difficulties relating to formulation in achieving relatively high sun protection factors or UV protection performance.

In particular, the formulation of the preparations with physical filters, such as $TiO_2$, is difficult and leads to instabilities.

It is furthermore disadvantageous that sun protection preparations frequently lose their protective effect after contact with water during bathing or swimming due to the "wash off" effect.

The object of the present invention is therefore to provide a sun protection preparation which, in addition to a cosmetic acceptance, has an improved water proofness on the skin.

SUMMARY OF THE INVENTION

The present invention provides a method of increasing the waterproofness of a cosmetic or dermatological preparation on human skin. The method comprises providing in the preparation at least one polyamide-5 compound in an amount that is effective for improving the waterproofness of the preparation on human skin.

In one aspect of the method, the preparation may be an emulsion and/or may comprise at least one UV filter substance. For example, the preparation may be a W/O or W/S emulsion that comprises at least one UV filter substance.

In another aspect, the preparation may comprise one or more substances selected from anti-wrinkle substances, skin moisturizing agents, and lipids.

The present invention also provides a method of increasing the long-term stability below 15° C. of a cosmetic or dermatological preparation. The method comprises providing in the preparation at least one polyamide-5 compound in an amount that is effective for improving the long-term stability of the preparation below 15° C.

In one aspect of the method, the preparation may be an emulsion.

In another aspect, the preparation may comprise at least one substance selected from UV filter substances, anti-wrinkle substances, skin moisturizing agents, and lipids.

The present invention also provides a method of reducing the stickiness a cosmetic or dermatological preparation and/or of increasing the skin moisturization by a cosmetic or dermatological preparation that comprises at least one skin humectant and/or at least one polar lipid and/or of improving the dispersibility on skin of a cosmetic or dermatological preparation that comprises at least one lipid. The method comprises providing in the cosmetic or dermatological preparation at least one polyamide-5 compound in an amount that is effective for reducing the stickiness of the preparation and/or for increasing the skin moisturization by the preparation and/or for improving the dispersibility of the preparation on skin.

In one aspect of the method, the preparation may be an emulsion.

In another aspect, the preparation may comprise at least one substance selected from UV filter substances, anti-wrinkle substances, skin moisturizing agents, and lipids.

DETAILED DESCRIPTION OF THE INVENTION

It was surprising and not foreseeable to one skilled in the art that the use of one or more polyamide-5 compounds helps to increase the care and/or efficacy properties of cosmetic or dermatological preparations.

The preparations advantageously comprise one or more treatment substances and/or active substances selected from the group of UV filter substances, anti-wrinkle ingredients, skin moisturizing agents and/or lipids.

According to the invention, the care or efficacy property is seen to be primarily water proofness, skin moisturizing, wrinkle reduction and long-term stability. The following substances, which are responsible for the respective effects, are listed as corresponding active ingredients or care substances.

Surprisingly, however, the efficacy can be increased after the addition of polyamide-5 compounds, or with the same efficacy the proportion of active substances or care substances can be reduced.

As is known, one or more polyamide-5 compounds can be used to increase the sun protection factor and/or the UV protection effect of cosmetic or dermatological sunscreen agents, which contain at least one UV filter substance. However, it was surprisingly shown that one or more polyamide-5 compounds can be used to increase the waterproofness of the preparation, in particular, W/O or W/S emulsions containing sunscreen filters, on human skin, which thus indirectly likewise help to increase the light protection efficiency of the preparation.

The increase of the skin moisture by the use of one or more polyamide-5 compounds in cosmetic or dermatological preparations comprising at least one skin moisturizing agent and/or polar lipid, can also be observed.

The cosmetic and dermatological preparations in the sense of the present invention do not leave a greasy or sticky impression on the skin and are extremely well tolerated by the skin, which is shown by the advantageous distribution of care substances and active substances in the preparation by polyamide-5 compounds.

The increase of the care and/or efficacy properties means according to the invention the increase in the care and/or efficacy properties caused by the care substances or active substances contained compared to a preparation containing the same ingredients without the polyamide-5 compounds.

The Orgasol Caresse®, the polyamide-5 compounds according to the invention, is a fine polyamide copolymer (6-12) powder, which produces an improvement of the feeling on the skin above all in aqueous systems, especially O/W emulsions.

The particle size is approx. 10 μm. Compared to the other Orgasol types, Orgasol Caresse has a higher absorption capacity (oil as well as water).

In addition to improving the feeling on the skin, Orgasol Caresse, has other properties:

Improved dispersibility of the emulsion

Higher absorption capacity than the other types

Gives the emulsion a certain richness, even with a small oil phase

Better dispersibility of sunscreen pigments in sunscreen products

Renders possible a soft focus effect

Compatible with higher concentrations of electrolytes

Compatible with ethanol

According to the invention, these compounds are referred to as polyamide-5 compounds.

The sunscreen preparations according to the invention can be composed as usual. They preferably comprise UV filter substances based on triazine derivatives. These UV filters, which have the structural feature

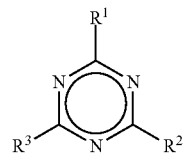

are known per se and are described, for example in EP-A-775 698, EP-A-0 878 469 and EP-A-1 027 881.

With respect to the $C_3$ axis of the triazine parent substance of these compounds, symmetrical substitution as well as asymmetrical substitution are conceivable. In this sense symmetrically substituted s-triazines have three identical substituents $R^1$, $R^2$ and $R^3$, whereas asymmetrically substituted s-triazine derivatives accordingly have different substituents, whereby the $C_3$ symmetry is destroyed. For the purposes of the present invention, "asymmetrical" always means asymmetrical with respect to the $C_3$ axis of the triazine parent substance, unless otherwise explicitly specified. Asymmetrically substituted s-triazine derivatives according to the invention are also referred to below simply as triazine derivatives.

Triazine derivatives according to the invention are therefore, for example, those that are described in EP-A-775 698:

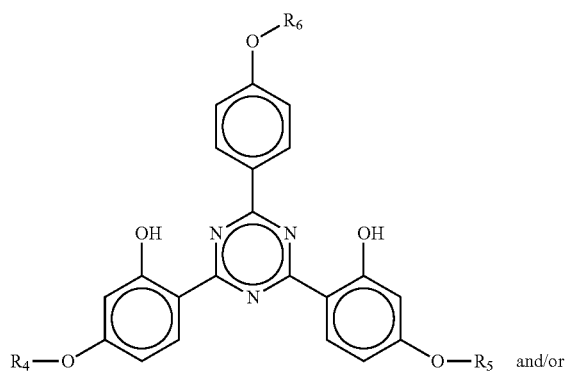

and/or

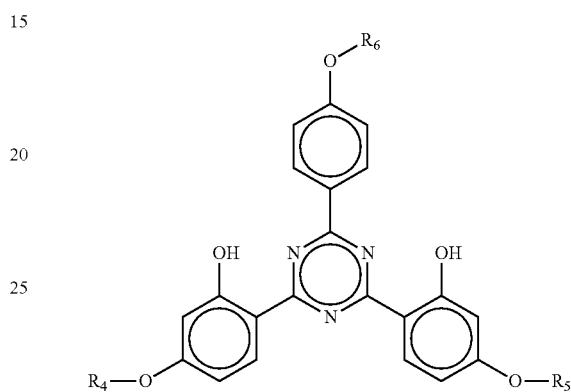

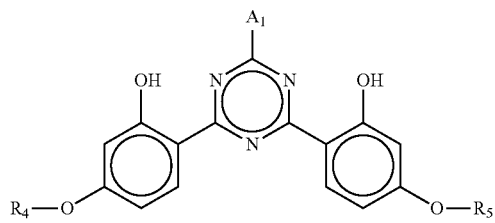

All of the bis-resorcinyltriazines mentioned in this document, whether disclosed generically or by concrete formulas, are advantageous for the purposes of the present invention.

Very particularly advantageously selected are $R_4$ and $R_5$ from the group of the branched and unbranched alkyl groups having 1 to 18 carbon atoms. The alkyl groups can also be advantageously substituted with silyloxy groups.

$A_1$ advantageously represents a substituted homocyclic or heterocyclic aromatic five-membered ring or six-membered ring.

The following asymmetrically substituted s-triazine compounds are very particularly advantageous for the purposes of the present invention:

where $R_6$ represents a hydrogen atom or a branched or unbranched alkyl group with 1 to 10 carbon atoms, in particular 2,4-bis-{[4-(2-ethylhexyloxy)-2-hydroxy]phenyl}-6-(4-methoxyphenyl)-1,3,5-triazine (INCI: Aniso Triazine), which is available under the trade name Tinosorb® S from CIBA-Chemikalien GmbH and is characterized by the following structure:

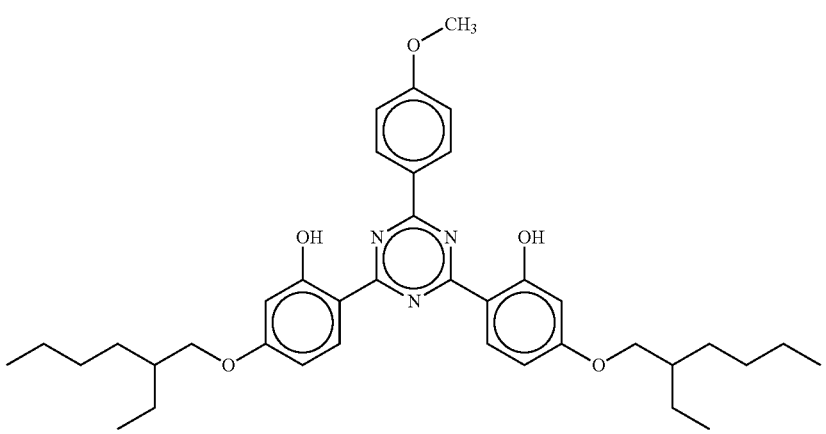

Another particularly advantageous asymmetrically substituted triazine derivative for the purposes of the present invention is dioctylbutyl amido triazone (INCI: dioctyl butamido triazone), which is available under the trade name UVASORB HEB from 3V Sigma and is characterized by the following structural formula:

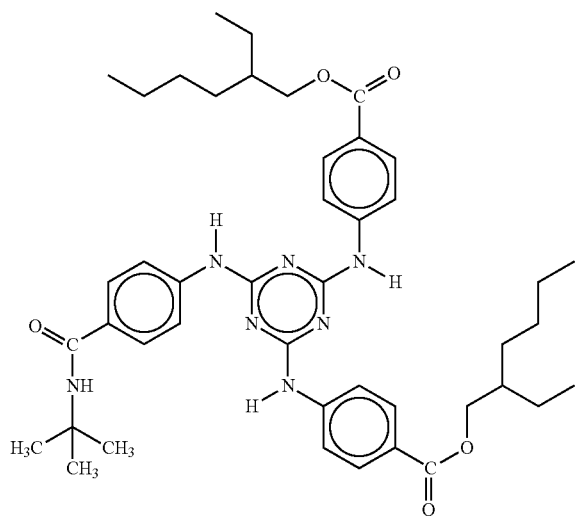

2,4-bis-(4'-di-neopentyl aminobenzalmalonate)-6-(4"-butyl aminobenzoate)-s-triazine

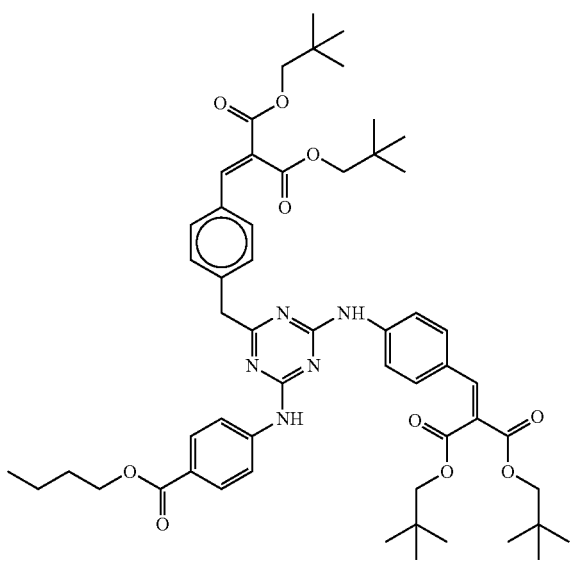

The following are also advantageous for the purposes of the present invention:
2,4-bis-{[4-(3-sulfonato)-2-hydroxy-propyloxy)-2-hydroxy]-phenyl}-6-(4-methoxyphenyl)-1,3,5-triazine sodium salt,
2,4-bis-{[4-(3-(2-propyloxy)-2-hydroxy-propyloxy)-2-hydroxy]-phenyl}6-(4-methoxyphenyl)-1,3,5-triazine,
2,4-bis-{[4-(2-ethyl-hexyloxy)-2-hydroxy]-phenyl}-6-[4-(2-methoxyethyl-carboxyl)-phenylamino]-1,3,5-triazine,
2,4-bis-{[4-(3-(2-propyloxy)-2-hydroxy-propyloxy)-2-hydroxy]-phenyl}-6-[4-(ethyl carboxyl)-phenylamino]-1,3,5-triazine,
2,4-bis-{[4-(2-ethyl-hexyloxy)-2-hydroxy]-phenyl}-6-(1-methyl-pyrrol-2-yl)-1,3,5-triazine,
2,4-bis-{ [4-tris(trimethylsiloxy-silylpropyloxy)-2-hydroxy]-phenyl}-6-(4-methoxy-phenyl)-1,3,5-triazine,
2,4-bis-{[4-(2"-methylpropenyloxy)-2-hydroxy]-phenyl}-6-(4-methoxyphenyl)-1,3,5-triazine and
2,4-bis-{[4-(1',1',1',3',5',5',5'-heptamethylsiloxy-2'-methyl-propyloxy)-2-hydroxy]-phenyl}-6-(4-methoxyphenyl)-1,3,5-triazine The asymmetrically substituted s-triazine derivative(s) according to the invention are advantageously incorporated into the oil phase of the cosmetic or dermatological formulations.

Further UV-A filter substance(s) of the preparations according to the invention is or are the phenylene-1,4-bis-(2-benzimidazyl)-3,3'-5,5'-tetrasulfonic acid

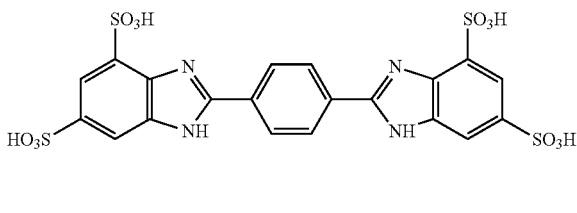

and the salts thereof, preferably the corresponding sodium, potassium or triethanolammonium salts, in particular the phenylene-1,4-bis-(2-benzimidazyl)-3,3'-5,5'-tetrasulfonic acid-bis-sodium salt

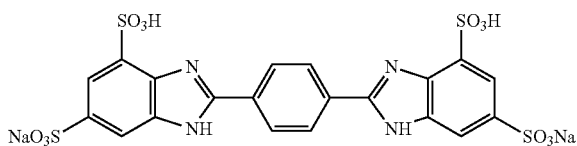

with the INCI designation bisimidazylate, which is available, for example, under the trade name Neo Heliopan AP from Haarmann & Reimer.

Moreover, according to the invention, the UVA filter diethylamino hydroxybenzoyl hexyl benzoate can be preferably used, which is available under the trade name Uvinul A Plus from BASF.

Furthermore, at least one UV filter substance can be selected from 2,2'-methylene-bis-(6-(2H-benzotriazole-2-yl)-4-(1,1,3,3-tetramethylbutyl)-phenol) [INCI: Bisoctyltriazol], which is characterized by the chemical structural formula

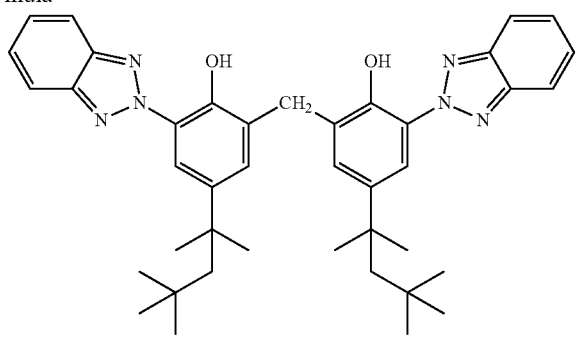

and is available under the trade name Tinosorb® M from CIBA Chemikalien GmbH.

Particularly advantageously, at least 2 of the listed UV filter substances are used together. Exemplary and advantageous combinations are:

2,4-bis-{[4-(2-ethyl-hexyloxy-)2-hydroxyl)-phenyl}-6-(4-methoxyphenyl)-1,3,5-triazine with phenylene-1,4-bis-(2-benzimidazyl)-3,3'-5,5'-tetrasulfonic acid-bis-sodium salt;

phenylene-1,4-bis(2-benzimidazyl)-3,3'-5,5'-tetrasulphonic acid-bis-sodium salt with 2,2'-methylene-bis-(6-(2H-benzotriazol-2-yl)-4-(1,1,3,3-tetramethylbutyl)-phenol) or 2,4-bis{[4-(2-ethyl-hexyloxy)-2-hydroxy]-phenyl}-6-(4-methoxyphenyl)-1,3,5-triazine with 2,2'-methylene-bis-(6-(2H-benzotriazol-2-yl)-4-(1,1,3,3-tetramethylbutyl) phenol).

Another embodiment of the present invention contains 2,4-bis{[4-(2-ethyl-hexyloxy)-2-hydroxy]-phenyl}-6-(4-methoxyphenyl)-1,3,5-triazine (Tinosorb® S), phenylene-1,4-bis-(2-benzimidazyl)-3,3'-5,5'-tetrasulphonic acid-bis-sodium salt (Neo Heliopan® AP) and 2,2'-methylene-bis-(6-(2H-benzotriazol-2-yl)-4-(1,1,3,3-tetramethylbutyl)-phenol) (Tinosorb® M) together as UV filter substances.

The above-referenced UV filter substances are advantageously present in total in quantities of from 0.1% by weight to 20% by weight, preferably 0.5% by weight to 15% by weight, in particular 1% to 10% by weight, in each case based on the total weight of the preparations.

Further conventional UV filter substances that can be used in the preparations according to the invention (optionally or additionally) are listed below:

Advantageous oil-soluble UV filters are, e.g.:
3-benzylidencamphor derivatives, preferably 3-(4-methyl-benzylidene)camphor [INCI: 4-methylbenzylidene camphor], which is sold by Merck under the tradename Eusolex 6300 and/or 3-benzylidene-camphor;
4-aminobenzoic acid derivatives, preferably 2-ethylhexyl 4-dimethylaminobenzoate, amyl 4-dimethylaminobenzoate;
esters of cinnamic acid, preferably 2-ethylhexyl 4-methoxycinnamate, isopentyl 4-methoxycinnamate;
esters of salicylic acid, preferably 2-ethylhexyl salicylate, 4-isopropylbenzyl salicylate, homomenthyl salicylate;
derivatives of benzophenone, preferably 2-hydroxy-4-methoxybenzophenone, 2-hydroxy-4-methoxy-4'-methylbenzophenone, 2,2'-dihydroxy-4-methoxybenzophenone;
esters of benzalmalonic acid, preferably di(2-ethylhexyl) 4-methyoxybenzalmalonate,
symmetrical triazine derivatives with regard to the $C_3$-axis of the parent substance, preferably tris(2-ethylhexyl) 4,4',4"-(1,3,5-triazine-2,4,6-triyltriimino)trisbenzoate, [INCI: Octyl Triazone], which is sold by BASF Aktiengesellschaft under the trade designation UVINUL® T 150,
benzotriazole derivatives, preferably 2,2'-methylene-bis-(6-(2H-benzotriazol-2-yl)-4-(1,1,3,3-tetramethylbutyl)phenol
and UV filters bonded to polymers.

Advantageous water-soluble UV-B filter substances are, e.g.:
salts of 2-phenylbenzimidazole-5-sulfonic acid, such as its sodium, potassium or its triethanolammonium salt, and the sulfonic acid itself;
sulfonic acid derivatives of 3-benzylidenecamphor, such as, for example, 4-(2-oxo-3-bornylidenemethyl)benzenesulfonic acid, 2-methyl-5-(2-oxo-3-bornylidene-methyl)sulfonic acid and its salts.

Further conventional UV-A filters that can be used in preparations according to the invention are, for example, derivatives of dibenzoylmethane, in particular 1-(4'-tert-butylphenyl)-3-(4'-methoxyphenyl)propane-1,3-dion and 1-phenyl-3-(4'-isopropylphenyl)propane-1,3-dion. An advantageous UV-A filter substance is also 4-(tert-butyl)-4'-methoxydibenzoylmethane (CAS No. 70356-09-1), which is sold by Givaudan under the trademark Parsol® 1789 and by Merck under the trade name Eusolex® 9020.

Furthermore 1,4-di(2-oxo-10-sulfo-3-bornylidenemethyl) benzene and salts thereof are advantageous (in particular the corresponding 10-sulfato compounds, in particular the corresponding sodium, potassium or triethanolammonium salt), which is also referred to as benzene-1,4-di(2-oxo-3-bornylidenemethyl-10-sulfonic acid) and is characterized by the following structure:

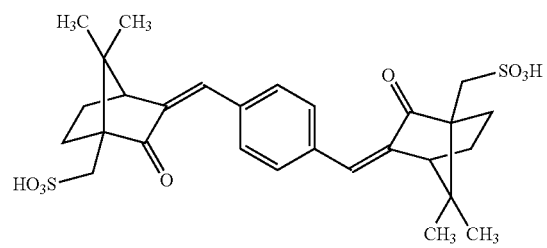 [SMILES: CC1(C)C2CCC1(CS(=O)(=O)O)C(=O)/C2=C\c1ccc(/C=C2\C(=O)C3(CS(=O)(=O)O)CCC2C3(C)C)cc1]

Advantageous filter substances that absorb UV-A a well as UV-B radiation, so-called broadband filters, are, e.g., 2,2'-methylenebis(6-(2H-benzotriazol-2-yl)-(1,1,3,3-tetramethylbutyl)phenol) or 2-(2H-benzotriazol-2-yl)-4-methyl-6-[2-methyl-3-[1,3,3,3-tetramethyl-1-[(trimethylsilyl)oxy] disiloxanyl]propyl]phenol (CAS No.: 155633-54-8) with the INCI designation Drometrizole Trisiloxane, which is characterized by the chemical structural formula

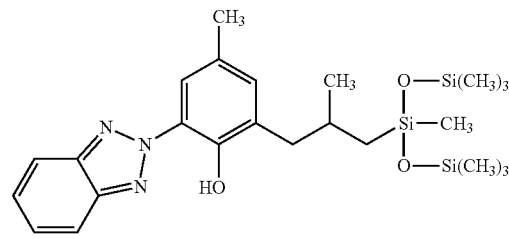

Furthermore, for example, certain salicylic acid derivatives such as 4-isopropyl benzyl salicylate, 2-ethylhexyl salicylate (=octyl salicylate), homomenthyl salicylate are suitable as UV filter substances.

Another sunscreen filter substance to be used advantageously according to the invention is 2-ethylhexyl 2-cyano-3,3-diphenylacrylate (Octocrylene), which is available from BASF under the designation Uvinul® N 539 and is characterized by the following structure:

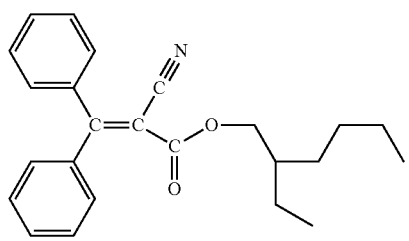 [SMILES: CCCCC(CC)COC(=O)C(C#N)=C(c1ccccc1)c1ccccc1]

Furthermore, the preparations according to the invention, when they are present in the form of so-called oil-free cosmetic or dermatological preparations, as preferably in this case, which contain an aqueous phase and at least one UV filter substance that is liquid at room temperature as a further phase, may contain the following UV filter substances that are liquid at room temperature.

Advantageous UV filter substances which are liquid at room temperature are homomenthyl salicylate, 2-ethylhexyl 2-cyano-3,3-diphenylacrylate, 2-ethylhexyl 2-hydroxybenzoate and esters of cinnamic acid, preferably 2-ethylhexyl 4-methoxycinnamate and isopentyl 4-methoxycinnamate.

Homomenthyl salicylate (INCI: Homosalate) is characterized by the following structure:

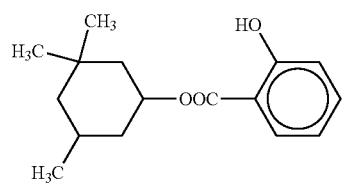

2-Ethylhexyl 2-cyano-3,3-diphenylacrylate (INCI: Octocrylene) is available from BASF under the name Uvinul® N 539 and is characterized by the following structure:

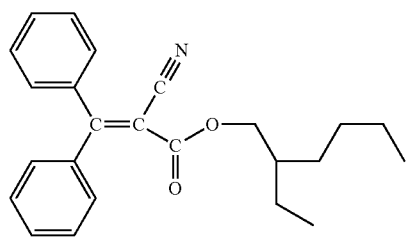 [SMILES: CCCCC(CC)COC(=O)C(C#N)=C(c1ccccc1)c1ccccc1]

2-Ethylhexyl-2-hydroxybenzoate (2-ethylhexyl salicylate, octyl salicylate, INCI: octyl salicylate) is available, for example, from Haarmann & Reimer under the trade name Neo Helipan OS and is characterized by the following structure:

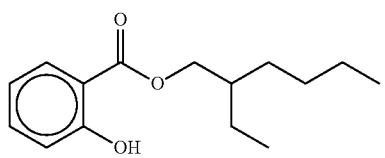

4-Methoxycinnamate 2-ethylhexyl ester(2-ethylhexyl-4-methoxycinnamate, INCI: octyl methoxycinnamate) is available from Hoffmann-La Roche, for example, under the trade name Parsol MCX and is characterized by the following structure:

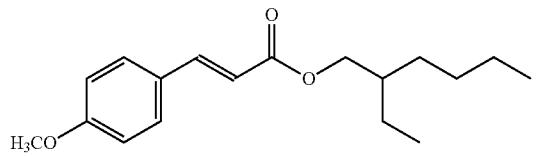 [SMILES: CCCCC(CC)COC(=O)/C=C/c1ccc(OC)cc1]

4-Methoxycinnamate isopentyl ester(isopentyl-4-methoxycinnamate, INCI: isoamyl p-methoxycinnamate) is available from Haarmann & Reimer, for example under the trade name Neo Heliopan E 1000 and is characterized by the following structure:

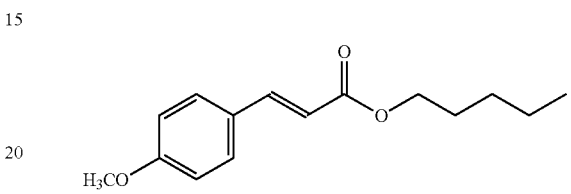

The total quantity of one or more UV filter substances which are liquid at room temperature in the finished cosmetic or dermatological preparations is advantageously selected from the range of 0.1% by weight to 30% by weight, preferably from 0.5% to 20% by weight, in each case based on the total weight of the preparations.

The list of the cited conventional UV filter substances that can be used for the purposes of the present invention is, of course, not intended to be limiting.

It is advantageous due to the increase in sunscreen protection of the preparations according to the invention if either higher SPF values are achieved with the preparations according to the invention compared to preparations with the same UV filter proportions without polyamide-5 compounds, or the same SPF values but then with reduced UV filter proportions.

The increase of the sunscreen protection by the polyamide-5 compounds is shown by the following comparative tests. Interestingly, the water proofness of the UV sunscreen preparations containing the polyamide-5 compound is also improved, as the tests below show.

Comparative tests—Test 27860; test for SPF and water proofness Comparison formulas:

| | Quantity in % by weight | |
|---|---|---|
| Ingredient | Formula 1 | Formula 2 |
| Cetyl PEG/PPG-10/1 Dimethicone | 0.5 | 0.5 |
| Cyclomethicone | 20 | 20 |
| Butylene glycol dicaprylate/dicaprate | 7 | 7 |
| BHT | 0.05 | 0.05 |
| Shea butter | 3 | 3 |
| VP/hexadecene copolymer | 0.5 | 0.5 |
| Sodium EDTA | 1 | 1 |
| Butyl methoxy dibenzoylmethane | 4.5 | 4.5 |
| Phenylbenzimidazole sulfonic acid; Sodium salt | 1.5 | 1.5 |
| Ethylhexyl salicylate | 1.5 | 1.5 |
| Octocrylene | 9 | 9 |
| Homosalate | 3.5 | 3.5 |
| Bis-ethylhexyloxyphenol methoxyphenyl triazine | 3.5 | 3.5 |
| Titanium dioxide + trimethoxycaprylylsilane | 2 | 2 |
| Glycerin | 6 | 6 |
| Water | 25.475 | 22.475 |

-continued

| Ingredient | Quantity in % by weight | |
|---|---|---|
| | Formula 1 | Formula 2 |
| Lauroyl lysine | 1 | 1 |
| Polymethylsilsesquioxane | 2.5 | 2.5 |
| Polyamide-5 (Orgasol Caresse) | 0 | 3 |
| Ethanol | 2 | 2 |
| Ethyl paraben | 0.2 | 0.2 |
| Methyl paraben | 0.2 | 0.2 |
| Phenoxyethanol | 0.4 | 0.4 |
| Methylpropanediol | 4 | 4 |
| Licorice root extract | 0.025 | 0.025 |
| Vitamin E acetate | 0.6 | 0.6 |
| Sodium hyaluronate | 0.05 | 0.05 |
| Total | 100 | 100 |

Methods:
Sun protection factor measurement:
The SPF (sun protection factor) is determined according to the specifications of the New International SPF Method (2006) in vivo on human skin (COLIPA).
Definition: SPF=quotient of minimal erythemal dose (MED) on protected and unprotected skin.
Sun protection/waterproofness measurement:
First the SPF is determined and on an additional area SPF determination after respectively 20 minutes wetting and 15 minutes drying time (2×20 min=water resistant, 4×20 min—extra water resistant, 18×20 min=water proof). It is water proof when the value after wetting is more than 50% of the previous SPF.
Results of the SPF value and the water proofness:

| Formula | SPF | Increase % | Waterproofness | Increase % |
|---|---|---|---|---|
| 1 | 55.6 | — | 38.0 | — |
| 2 | 70.2 | 26.25 | 43.7 | 15.0 |

Through the addition of the polyamide-5 compounds an unforeseeable increase in the sunscreen effect of UV sunscreen preparations can be obtained. Likewise through the addition of polyamide-5 compounds the waterproofness of these preparations is increased.

One or more polyamide-5 compounds (Orgasol Caresse) can thus be used to increase the SPF and/or the UV protection effect of cosmetic or dermatological sunscreen agents that contain at least one UV filter substance.

One or more polyamide-5 compounds (Orgasol Caresse®) can be used in cosmetic or dermatological sunscreen preparations to increase the water proofness of the preparation on the human skin.

The cosmetic and dermatological preparations according to the invention can also comprise cosmetic auxiliaries as are customarily used in such preparations, e.g. preservatives, preservative aids, bactericides, perfumes, substances for preventing foaming, dyes and pigments which have a coloring effect, thickeners, moisturizing and/or humectant substances, fats, oils, waxes, or other customary constituents of a cosmetic or dermatological formulation, such as alcohols, polyols, polymers, foam stabilizers, electrolytes, organic solvents or silicone derivatives.

Surprisingly, the following combinations with polyamide-5 compounds have proven to be very advantageous in cosmetic application.

Thus the combination of anti-wrinkle substances with polyamide-5 compounds (Orgasol Caresse®) leads to an immediate effect with the topical application of the preparation according to the invention containing them.

The filling of the lines or wrinkles with the spherical polyamide-5 (Orgasol Caresse®) globules and the loading thereof with anti-wrinkle substances leads to a permanent reduction of the wrinkles and their formation directly at the active location.

Further advantageous anti-wrinkle substances for the purposes of the present invention are natural active ingredients and/or derivatives thereof, such as, for example, alpha-lipoic acid, phytoene, D-biotin, coenzyme Q10, alpha-glucosylrutin, carnitine, carnosine, natural and/or synthetic isoflavonoids, creatine, fumaric esters, ectoin and derivatives thereof, tea extracts, folic acid, arginine and salts thereof, taurine and/or β-alanine. These active ingredients can be contained in the preparation in a proportion of from 0.001% to 10% by weight, based on the total weight of the preparation.

Due to the content of polyamide-5 compounds (Orgasol Caresse®) and the good dispersibility of the preparation on the skin associated therewith, the proportion of poorly spreading lipids can be reduced and the feeling on the skin thus further improved, accompanied by a reduced stickiness and a good dispersibility on the skin.

C12-15 alkylbenzoate, butylene glycol dicaprylate/dicaprate and all UV filters that are liquid at room temperature, as listed above, can be selected in particular as lipids.

Furthermore, humectants or so-called moisturizers can be advantageously combined with polyamide-5 compounds.

Moisturizers is the term used to designate substances or mixtures of substances which, following application or distribution on the surface of the skin, confer on cosmetic or dermatological preparations the property of reducing the moisture loss by the horny layer (also called transepidermal water loss (TEWL)) and/or have a beneficial effect on the hydration of the horny layer.

The proportion of skin moisturizing agents, also called moisturizers, is preferably in the range of from 5% to 15% by weight, based on the total mass of the preparation.

Advantageous moisturizers for the purposes of the present invention are in particular glycerol. However, lactic acid, butylene glycol, sorbitol, pyrrolidonecarboxylic acid, polymeric moisturizers from the group of polysaccharides which are soluble in water and/or swellable in water and/or gellable using water can also be used. Particularly advantageous are, for example, short-chain hyaluronic acid (<50,000 Dalton) and long-chain hyaluronic acid (>50,000 Dalton), chitosan and/or a fucose-rich polysaccharide, which is filed in Chemical Abstracts under the registry number 178463-23-5 and is available, for example, under the name Fucogel® 1000 from SOLABIA S.A.

With anhydrous oil preparations, polyamide-5 compounds lead to a surprising improvement of the moisturizing of the skin. Although body oils are good for the treatment of dry skin, they have a disadvantage due to an inadequate humectant effect. It was possible to improve this substantially based on the combination with polyamide-5 compounds.

The group of polar oils is to be considered in particular as oils, for example, from the group of the lecithins and the fatty acid triglycerides, especially the triglycerides of saturated and/or unsaturated, branched and/or unbranched alkanecarboxylic acids of a chain length of 8 to 24, in particular 12 to 18 C atoms. The fatty acid triglycerides can advantageously be chosen, for example, from the group of the synthetic, semi-synthetic and natural oils, such as, for example, coconut glyceride, olive oil, sunflower oil, jojoba oil, soybean oil, peanut oil, rapeseed oil, almond oil, palm oil, coconut oil, castor oil, wheatgerm oil, grapeseed oil, thistle oil, evening primrose oil, macadamia nut oil and the like, as well as propylheptyl octanoate and/or diisopropyl sebacate.

Further advantageous polar oil components for the purposes of the present invention may further be selected from the group of the esters of saturated and/or unsaturated, branched and/or unbranched alkanecarboxylic acids of a chain length of 3 to 30 C atoms and saturated and/or unsaturated, branched and/or unbranched alcohols of a chain length of 3 to 30 carbon atoms, and from the group of the esters of aromatic carboxylic acids and saturated and/or unsaturated, branched and/or unbranched alcohols of a chain length of 3 to 30 C atoms. Such ester oils can then advantageously be chosen from the group of phenethyl benzoate, 2-phenylethyl benzoate, isopropyl lauroyl sarcosinate, phenyl trimethicone, cyclomethicone, dibutyladipate, octyl palmitate, octyl cocoate, octyl isostearate, octyldodecyl myristate, octyldodecanol, cetearyl isononanoate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, stearyl heptanoate, oleyl oleate, oleyl erucate, erucyl oleate, erucyl erucate, tridecyl stearate, tridecyl trimellitate, and also synthetic, semi-synthetic and natural mixtures of such esters, such as, for example, jojoba oil, acetyl trifluoromethylphenyl valylglycine, acrylamide ammonium acrylate copolymer, aluminum magnesium hydroxide stearate, ammonium lactate, ammonium polyacrylate, ammonium polyacryloyldimethyl taurate, arginine PCA, caproyloyl salicylic acid ester, cinnamic acid, cocoglucoside, copper gluconate, diphenyldimethicone, disodium adenosine triphosphate, disodium succinate, disteardimonium hectorite, dodecene, eperua falcata, hydrogenated palm glyceride, hydrogenated palm glyceride citrate, hydrogenated palm kernel glycerides, hydrolyzed wheat protein, PG propyl methyl silanediol, hydroxyethyl acrylate/sodium acryloyldimethyltaurate copolymer, isodeceth-6, linseed acid magnesium aspartate, melibiose, oxothiazolidine carboxylic acid, palmitoyl pentapeptide 4, PEG-8 laurate, phenethylalcohol, phenyl propanol, polyacrylate-13, polyacrylate-3, sarcosine, saxifraga sarmentosa extract, scutellaria baicalensis extract, sodium metabisulfite, soybean isoflavone, tocopherylglucoside, trideceth-6, and zinc gluconate.

The advantageous lipids and oils, referred to simply as lipids, are better distributed or held in the cosmetic preparation by polyamide-5 and thus lead to the observed improvements in effectiveness, such as skin moisturizing.

In particular W/O emulsions, O/W emulsions, hydrodispersions, gels, alcoholic preparations, cosmetic sprays, pads, wipe, plaster, W/S, S/W, microemulsion, nanoemulsion, mousse, foam, PIT emulsion, oil, hydrogel, hydrodispersion gel, oleogel, S/W, W/S, multiple emulsion, ointment, cream gel, cream lotion are formulated with polyamide-5 compounds as preparations according to the invention.

The preparations according to the invention may be advantageously formulated as an aerosol, pump spray, tube, pot, bag-in-can system, ampoule, as a kit of different types of packaging, to fill electrically operated, storage battery-operated and battery-operated devices.

Furthermore, in particular the use of one or more polyamide-5 compounds in W/O or W/S emulsions containing sunscreen filters has proven to be useful, when these preparations are available in a packaging that contains a ball for better removal of the preparation.

In order to improve the dispersibility of W/O emulsion preparations, in the prior art frequently silicone oils, nonpolar mineral oils and polar lipids such as isopropyl palmitate are used. However, this often results in a slight to heavy oil separation as well as a low-temperature instability of the preparation containing these oils.

Through the use of polyamide-5 it was possible to substantially increase the stability of these preparations in the direction of reduced oil separation and improved temperature stability ($<15°$ C.).

The preparation according to the invention comprising polyamide-5 compounds can thus be used for the care/treatment of hands, elbows, knees, feet, face, nails, cuticles, breast tightening, breast lifting, pregnancy and stretch marks, nipples during nursing, lips, eyes, hair, as skin disinfectant, for skin lightening, application in the shower or as a bath product, as a carrier of repellents, as the base for makeup products, enriched with particles as a scrub, since it provides the corresponding active ingredients or care substances in a targeted manner at the action site.

In conclusion, surprisingly it can be established that the polyamide-5 compounds according to the invention lead to an improved distribution of active ingredients, such as e.g., anti-wrinkle ingredients and care substances, such as, e.g., oils, in cosmetic preparations. The better dispersibility then in turn leads to an improved stability as well as to better product performance. Thus with the same effectiveness, for example, the low-temperature stability ($<15°$ C.), less active ingredients or stabilizing agents can be used than the preparations without polyamide-5 compounds. The proportion of active substances can thus be reduced without adverse effects in terms of efficacy.

With the same proportion of active ingredients or care substances, in turn an increased effectiveness compared to preparations without polyamide-5 compounds is found (see, e.g., the sun protection efficiency or waterproofness).

In sunscreen preparations, these nylon types help the polyamide-5 compounds to avoid the formation of white residues, which likewise indicates an improved dispersion and stabilization of substances in the preparations.

The following examples explain preparations according to the invention. The listed figures represent weight percentages, based on the total mass of the preparations.

| Example | 1 | 2 | 3 | 4 | 5 | 6 |
|---|---|---|---|---|---|---|
| Glyceryl stearate citrate | 2 | 2 | 3 | | | |
| Glyceryl stearate SE | | | | 1 | 1 | 1.5 |
| Cetearyl alcohol + PEG-40 castor oil + sodium cetearyl sulfate | | | | 2.5 | 2.5 | 3 |
| Cetearyl alcohol | | | | 1 | 1 | |
| Stearyl alcohol | 0.5 | | | | | 2 |
| Myristyl myristate | 1.0 | 1 | | | 3 | |
| Acrylates/$C_{10-30}$ alkyl acrylate crosspolymer | 0.1 | 0.2 | | | 0.1 | |

-continued

| Example | 1 | 2 | 3 | 4 | 5 | 6 |
|---|---|---|---|---|---|---|
| Carbomer | | 0.2 | 0.3 | 0.2 | | |
| Xanthan gum | 0.4 | | 0.2 | 0.2 | 0.3 | 0.4 |
| $C_{12-15}$ Alkyl benzoate | | 3 | | | 5 | |
| Butylene glycol dicaprylate/dicaprate | 5 | | | | 3 | 3 |
| Methylpropanediol | | 1 | | 0.5 | | |
| 1,2-Hexanediol | 0.2 | | 0.1 | 0.3 | 0.1 | 0.1 |
| 1,2-Octanediol | | 0.2 | 0.1 | | 0.3 | |
| Cyclomethicone | | | | 5 | 10 | |
| PVP Hexadecene copolymer | | 0.5 | | | | 1 |
| Propylene glycol | | | 1 | | 5 | 3 |
| Glycerin | 7.5 | 5 | 7 | 10 | 13 | 3 |
| Alcohol denat. | 2 | 3 | | 7 | | |
| Titanium dioxide | 3 | | | 2 | | 3 |
| Ethylhexyl triazine | 2.5 | 2 | | 1 | | |
| 2-Ethylhexyl 4-methoxycinnamate | | 5 | | 2 | | |
| Octocrylene | 7.5 | 8 | 3 | 2 | 2 | 1 |
| Butylmethoxy dibenzoylmethane | 3.8 | 4 | 3.5 | 2 | | |
| Phenylbenzimidazole sulfonic acid | | | | 2.5 | 3 | 2 |
| Hexyl 2-(4'-diethylamino-2'-hydroxybenzoyl)-benzoate | | 2 | | 3 | 5 | 10 |
| 2,2'-Methylene-bis-(6-(2H-benzotriazole-2-yl)-4-(1,1,3,3-tetramethylbutyl)-phenol | | 4 | | | 2 | |
| 2,4,6-Tris-(biphenyl)-1,3,5-triazine | | | 1 | 3 | | |
| Polyamide-5 | 2.5 | 4 | 3 | 6 | 5 | 3.5 |
| Ethylhexyl salicylate | 2 | | 0.5 | 4 | 2.5 | |
| Bis-ethylhexyloxyphenol methoxyphenyl triazine | 2 | 1 | | 1 | | 1 |
| Vitamin E acetate | 0.2 | 0.2 | 0.2 | 0.3 | 0.1 | 0.5 |
| $Na_2H_2EDTA$ | 0.1 | 0.1 | 0.2 | 0.2 | 0.2 | 0.5 |
| Perfume, preservatives | q.s. | q.s. | q.s. | q.s. | q.s. | q.s. |
| Dyes, etc. | q.s. | q.s. | q.s. | q.s. | q.s. | q.s. |
| Citric acid, sodium citrate | q.s. | q.s. | q.s. | q.s. | q.s. | q.s. |
| Sodium hydroxide | q.s. | q.s. | q.s. | q.s. | q.s. | q.s. |
| Water | ad 100 | ad 100 | ad 100 | ad 100 | ad 100 | ad 100 |

What is claimed is:

1. A method of increasing the waterproofness of a cosmetic or dermatological preparation on human skin, wherein the method comprises providing in the preparation at least one polyamide-5 compound in an amount that is effective for improving the waterproofness of the preparation on human skin.

2. The method of claim 1, wherein the preparation is a W/S emulsion or a W/O emulsion.

3. The method of claim 2, wherein the W/S emulsion or W/O emulsion comprises at least one UV filter substance.

4. The method of claim 3, wherein the at least one UV filter substance comprises a triazine compound.

5. The method of claim 3, wherein also the sun protection factor of the preparation is increased.

6. The method of claim 2, wherein the preparation is a W/O emulsion.

7. The method of claim 3, wherein the preparation is a W/O emulsion.

8. The method of claim 1, wherein the preparation comprises at least one substance selected from anti-wrinkle substances, skin moisturizing agents, and lipids.

9. The method of claim 8, wherein the preparation comprises glycerol.

10. A method of increasing the long-term stability below 15° C. of a cosmetic or dermatological preparation, wherein the preparation is a W/O emulsion or a W/S emulsion and the method comprises providing in the preparation at least one polyamide-5 compound in an amount that is effective for improving the long-term stability of the preparation below 15° C.

11. The method of claim 10, wherein the preparation comprises at least one UV filter substance.

12. The method of claim 10, wherein the preparation is a W/O emulsion.

13. A method of increasing skin moisturization by a cosmetic or dermatological preparation that comprises at least one skin humectant and/or at least one polar lipid, wherein the method comprises providing in the cosmetic or dermatological preparation at least one polyamide-5 compound in an amount that is effective for increasing the skin moisturization by the preparation.

14. The method of claim 13, wherein the preparation comprises at least one UV filter substance.

15. The method of claim 13, wherein the preparation is an emulsion.

16. The method of claim 13, wherein the preparation is a W/O emulsion or a W/S emulsion.

17. The method of claim 13, wherein the preparation is an anhydrous oil preparation.

18. The preparation of claim 13, wherein the preparation comprises at least one skin humectant.

19. The preparation of claim 13, wherein the preparation comprises glycerol.

20. The preparation of claim 13, wherein the preparation comprises at least one polar lipid.

* * * * *